United States Patent [19]

Mandel

[11] Patent Number: 5,514,663
[45] Date of Patent: May 7, 1996

[54] SENNA DOSAGE FORM

[75] Inventor: Kenneth G. Mandel, Fairfield, Ohio

[73] Assignee: The Procter & Gamble Company, Cincinnati, Ohio

[21] Appl. No.: 138,859

[22] Filed: Oct. 19, 1993

[51] Int. Cl.⁶ ............................ A61K 31/70; A61K 35/78
[52] U.S. Cl. .............................. 514/33; 514/25; 514/892; 536/41; 536/18.1; 424/195.1
[58] Field of Search ........................... 424/195.1; 514/33, 514/892, 25; 536/17.3, 17.5, 18.1, 118, 4.1

[56] References Cited

U.S. PATENT DOCUMENTS

| | | | |
|---|---|---|---|
| 4,432,966 | 2/1984 | Zeitoun et al. | 424/21 |
| 4,511,561 | 4/1985 | Madaus et al. | 424/195.1 |
| 4,595,592 | 6/1986 | Hietala | 424/195.1 |
| 4,687,667 | 8/1987 | Rhodes et al. | 424/195.1 |
| 4,801,458 | 6/1989 | Hidaka et al. | 424/443 |
| 4,950,689 | 8/1990 | Yang et al. | 514/777 |
| 4,990,340 | 2/1991 | Hidaka et al. | 424/449 |
| 5,096,714 | 3/1992 | Kuhrts | 424/439 |
| 5,108,758 | 4/1992 | Allwood et al. | 424/468 |
| 5,178,866 | 1/1993 | Wright et al. | 424/473 |
| 5,232,699 | 8/1993 | Colliopoulos | 424/195.1 |
| 5,292,518 | 3/1994 | Kuhrts | 424/439 |
| 5,294,448 | 3/1994 | Ring et al. | 424/497 |

FOREIGN PATENT DOCUMENTS

| | | | |
|---|---|---|---|
| 1121215 | 12/1989 | Japan . | |
| 92/07553 | 5/1992 | WIPO | A61K 9/20 |
| 94/10983 | 5/1994 | WIPO | A61K 9/30 |

OTHER PUBLICATIONS

Dreessen, M., H. Eyssen and J. Lemli "The Metabolism of Sennosides A and B by the Intestinal Microflora: in Vitro and In Vivo Studies on the Rat and the Mouse" *J. Pharm. Pharmacol.*, vol. 33 (Apr. 16, 1981), pp. 679–681.

Fioramonti, J., G. Staumont, R. Garcia-Villar, L. Buéno "Effect of Sennosides on Colon Motility in Dogs" *Pharmacology*, vol. 36 (1988), suppl. 1, pp. 23–30.

Frexinos, J., G. Staumont, J. Fioramonti, and L. Buëno "Effects of Sennosides on Colonic Myoelectrical Activity in Man" *Digestive Diseases and Science*, vol. 34, No. 2 (Feb. 1989), pp. 214–219.

Garcia-Villar, R., E. Leng-Peschlow, and Y. Ruckebusch "Effect of Anthraquinone Derivatives on Canine and rat intestinal Motility" *Pharm. Pharmacol.* vol. 32 (1980), pp. 323–329.

Hardcastle, J. D. and J. L. Wilkins "The Action of Sennosides and Related Compounds on Human Colon and Rectum" *Gut.*, vol. 11 (Dec. 1970), pp. 1038–1042.

Lemli, J. and Lemmens "Metabolism of Sennosides and Rhein in the Rat" *Pharmacology*, vol. 20, (Suppl. 1) (1980), pp. 50–57.

Leng-Peschlow, E. "Acceleration of Large Intestine Transit Time in Rats by Sennosides and Related Compounds" *J. Pharm. Pharmacol.*, vol. 38 (1986), pp. 369–373.

Leng-Peschlow, E. "Dual Effect of Orally Administered Sennosides on Large Intestine Transit and Fluid Absorption in the Rat" *J. Pharm. Pharmacol.*, vol. 38 (1986), pp. 606–610.

Leng-Peschlow, E. "Effects of Sennosides A+B and Bisacodyl on Rat Large Intestine" *Pharmacology*, vol. 38 (1989) pp. 310–318.

Leng-Peschlow, E. "Effect of Sennosides and Related Compounds on Intestinal Transit in the Rat" *Pharmacology*, vol. 36 (1988) (Suppl. 1), pp. 40–48.

Staumont, G., J. Frexinos, J. Fioramonti and L. Buéno "Sennosides and Human Colonic Motility" *Pharmacology*, vol. 36 (Suppl. 1) (1988), pp. 49–56.

Wienbeck, M. E. Kortenhaus, M. Wallenfels and M. Karaus "Effect of Sennosides on Colon Motility in Cats" *Pharmacology*, vol. 36 (Suppl. 1) (1988) pp. 31–39.

Ambrose et al. *Br. J. Surg.* vol. 70: 428–430, (1983).

Ziegenhagen et al. *Gastrointestinal Endoscopy* vol. 37 (5): 547–549, (1991).

Iida et al. *Gastroenterologia Japonica* vol. 27(6): 728–733, (1992).

*Primary Examiner*—Douglas W. Robinson
*Assistant Examiner*—Howard C. Lee
*Attorney, Agent, or Firm*—Betty J. Zea; Karen F. Clark; Jacobus C. Rasser

[57] ABSTRACT

This invention relates to a pharmaceutical laxative composition in unit dosage form, for peroral administration of sennosides to a human or other animal subject, comprising a safe and effective amount of sennosides in a rapidly dissolving matrix; and a proximal colonic delivery carrier which effects release of said sennosides substantially near the junction between the small intestine and the colon or within the colon of said subject. This invention also involves methods for providing laxation for humans and other animals in need thereof by peroral administration of such compositions.

12 Claims, No Drawings

SENNA DOSAGE FORM

TECHNICAL FIELD

This invention involves a novel dosage form of senna, or sennosides, for providing laxation in the colon.

BACKGROUND OF THE INVENTION

Senna is a known active ingredient for use as a laxative. Senna is an extract of the senna plant. The extract primarily comprises sennosides A+ B. Sennosides A and B (sennosides, 5,5'-bis(β-D-glucopyranosyloxy)-9,9', 10,10'-tetrahydric- 4,4'-dihydroxy-10, 10'-dioxo[ 9,9'-bianthracene ]-2,2'-dicarboxylic acid) are stereoisomeric bisanthrone glucosides. In addition, other sennosides (named sennosides C, D, E, etc.) have been identified which can have laxative action. Although these other sennosides are minor components, they are a part of natural senna extracts. The preferred source of Ca-sennosides is partially purified extracts from dried leaves of "Indian senna" (*Cassia angustifolia*) or "African senna" (*Cassia acutifolia: Cassia senna*), and commonly prepared as calcium salts. Other natural sources include extracts of rhubarb, aloe, aloin. However, these latter have a relatively low content of sennosides and are higher in contaminants. Standardized senna concentrates are another available form for sennosides, but would be less preferred as a source of sennosides. Standardized senna extracts are obtained from dried seed pods, and generally have a lower concentration of sennosides than available from semipurified calcium sennosides.

Calcium sennosides and standardized senna concentrates are commercially available. One source of commercially available calcium sennosides is Huhtamaki Leiras (Finland). The product is labeled as 60% Casennosides, contains 72.3% sennosides by analysis according to the U.S. Pharmacopia (Volume XXII, 1990, page 1246).

The sennosides themselves have little to no direct laxative activity. Rather, they are convened to the derived active moiety, rhein-9-anthrone, by colonic bacteria. Pharmacology studies demonstrate that rhein-9-anthrone has the greatest purgative action associated with use of sennosides. Senna extracts and sennosides are water soluble. Sennosides are poorly absorbed from the small intestine, but the hydrolysis products generated in the colon (e.g., rhein or rhein-9-anthrone) are readily absorbed from both the small intestine and the colon.

Contact of the rhein with the mucosa produces increased propulsive peristaltic contractions of the colon which accelerate movement of contents through the colon. Since rhein acts upon contact with lumenal mucosa of the large intestine, its laxative effect is dependent upon generation of sufficient levels of the drug in the lumen of the colon.

Commercially available laxative whose active ingredient is senna, or sennosides, are in dose forms which deliver senna to the stomach or to the small intestine. At doses which produce maximal laxation, the sennosides also evoke secondary episodes of diarrhea.

Applicant has surprisingly discovered that delivery of sennosides to the colon as a rapidly dissolving matrix, or in a solubilized form, produces maximal laxation at doses lower than those found in commercial laxatives. Applicant has also surprisingly discovered that sennosides delivered to the colon are effective at doses which result in diminished secondary episodes of diarrhea relative to duodenally delivered senna.

SUMMARY OF THE INVENTION

This invention relates to a pharmaceutical laxative composition in unit dosage form, for peroral administration of sennosides to a human or other animal subject, comprising a safe and effective amount of sennosides in a rapidly dissolving matrix; and a proximal colonic delivery carrier which effects release of said sennosides substantially near the junction between the small intestine and the colon or within the colon of said subject.

This invention also involves methods for providing laxation for humans and other animals in need thereof by peroral administration of such compositions.

DETAILED DESCRIPTION OF THE INVENTION

The methods and compositions of this invention comprise a safe and effective amount of sennosides. As used herein, "sennosides" refers to senna extracts, Ca-sennosides, senna concentrates, and sennosides A+B. The term "safe and effective amount", as used herein, means an amount of sennosides high enough to provide a significant positive modification of the condition to be treated, but low enough to avoid serious side effects (at a reasonable benefit/risk ratio), within the scope of sound medical judgment. A safe and effective amount of sennosides will vary with the particular condition being treated, the age and physical condition of the patient being treated, the severity of the condition, the duration of the treatment, the nature of concurrent therapy and like factors. An effective dose of sennosides in compositions of this invention is preferably substantially lower than the dose of sennosides required to achieve efficacy with conventional sennosides-containing compositions.

A safe and effective dose of sennosides in a composition of this invention preferably provides from about 1 mg to about 100 mg of sennosides locally to the lumen of the lower gastrointestinal tract near the junction between the small intestine and or within the colon of a human patient. A preferred amount of sennosides dosed to a human patient is from about 1 mg to about 25 rag; more preferred is from about 1 mg to about 15 rag; more preferred still is from about 3 mg to about 10 mg. A unit dosage form of this invention preferably contains a single dose of sennosides in the above amounts. Generally, no more than about 100 mg of sennosides should be ingested by a single patient in any given day.

A pharmaceutical laxative composition dosage form of this invention for peroral administration of sennosides to a human or other animal subject comprises two functional pads: (a) a safe and effective amount of sennosides in a rapidly dissolving matrix; and (b) a proximal colonic delivery carrier which effects release of said sennosides substantially near the junction between the small intestine and the colon or within the colon of said subject. As used herein, "near the junction between the small intestine and the colon" means within the intestinal tract close to but on either side of the juncture joining the small intestine with the large intestine; this also includes release within the proximal colon. As used herein, "colon" refers to the portion of the large intestine which extends from the juncture with the small intestine up to but not including the rectum. The sennosides may be released near the junction between the small intestine and the colon, within the transverse colon, or within the descending colon. Preferably, the sennosides are released substantially near the junction between the small intestine and the colon.

Sennosides Matrix

As used herein, "sennosides matrix" is sennosides in a physical form or composition from which sennosides rapidly dissolves in the intestinal juices. This preferably consists of solid sennosides having a mean particle size below about 100μm. AS used herein, "rapidly dissolve" means dissolve substantially completely within from about 1 minute to about 20 minutes once dissolution commences.

A preferred sennosides matrix is comprised of a solid dispersion of sennosides in a water-soluble carrier such as polyethylene glycol (molecular weight greater than about 1000 daltons), poloxamer, citric acid, tartaric acid, dextrose monohydrate, or urea. Preferably substantially all of the sennosides in certain compositions of this invention is incorporated in such solid dispersions. Typical ratios (weight:weight) of water soluble carrier to sennosides range from about 1:1 to about 20:1. The solid dispersions may be prepared by a number of techniques well known to those skilled in the art, such as solvent evaporation, melt, spray drying, or freeze drying. The solvent evaporation technique involves dissolution of both the water-soluble carrier and sennosides in a volatile solvent which is then removed by evaporation or spray drying. The melt technique involves preparation of a melt of the water-soluble carrier and sennosides followed by solidification to produce a solid which may then be granulated. Aqueous or aqueous/water miscible solvent solutions of the water-soluble carrier and sennosides may also be prepared and either spray dried or lyophilized to produce a solid dispersion. Preferred water soluble carriers are those which are also solvents for sennosides, such as polyethylene glycol. Such solid dispersions are preferably incorporated into the unit dosage form as solid particulates, preferably less than about 1 mm in diameter.

The sennosides matrix can comprise, in addition to the preceding rapidly-dissolving or solubilized preparations of sennosides, excipients which improve the performance of the sennosides matrix. Such additional components may include, for example, dispersants which help disperse the sennosides in the gastrointestinal juices to aid in the rapid dissolution of the sennosides. Other optional components include preservatives, stabilizers, materials for facilitating the manufacture of the dosage form, and other excipients.

The sennosides matrix may comprise a powder of sennosides, or granulated solid dispersion that is encapsulated in a hard gelatin capsule that is subsequently coated with the proximal colonic delivery carrier. The sennosides powder composition may also include various excipients such as diluents (e.g., lactose, sucrose, starch, calcium sulfate, dicalcium phosphate, microcrystalline cellulose); binders (e.g., polyvinylpyrrolidone, pregelatinized starch, gelatin, hydroxypropyl methylcellulose, methylcellulose, hydroxyethyl cellulose, hydroxypropyl cellulose); lubricants (e.g., stearic acid, magnesium stearate); disintegrants (e.g., sodium starch glycolate, cross-linked polyvinylpyrrolidone, cross-linked carboxymethyl cellulose); gildants (e.g., fumed silica); and buffers. The powder mixture may be prepared via a number of techniques well-known to pharmaceutical science such as dry mixing, wet granulation, and fluid bed granulation. The solids mixture may be prepared via a number of techniques well-known to pharmaceutical science such as dry mixing, wet granulation, and fluid bed granulation, and be filled into capsules or compressed into tablets using conventional equipment and processes. Any compressed tablet preferably is made such that it rapidly disintegrates in intestinal juices.

The sennosides matrix may comprise a solid dispersion of sennosides and a water soluble carrier that is filled as a melt into hard or soft elastic gelatin (SEG) capsules that are subsequently coated with the proximal colonic delivery carrier. The sennosides matrix may comprise a compressed sennosides tablet. The compressed tablet preferably is made such that it rapidly disintegrates in intestinal juices. It may include any of the excipients listed for powder compositions above. Said tablets are subsequently coated with the proximal colonic delivery carrier.

Proximal Colonic Delivery Carrier

In the compositions of this invention, the proximal colonic delivery carrier prevents the release of sennosides as the dosage form passes through the upper gastrointestinal tract, including the mouth, esophagus, stomach, and small intestine, until the dosage form is near the junction between the small intestine and the colon or is in the colon.

As used herein, "proximal colonic delivery carrier" is a material or materials which encases the sennosides matrix in a manner that provides a dosage form for peroral ingestion. As such, the proximal colonic delivery carrier can consist of coating technologies encasing conventional tablets or capsules, specifically designed shells of capsules, or of other technologies which will prevent release and lumenal exposure of sennosides as the dosage form passes through the upper regions of the GI tract.

Enteric Coatings

Three types of proximal colonic delivery carrier are preferred. The first is a coating or covering applied to conventional dosage forms comprising the sennosides matrix such as compressed tablets, hard gelatin capsules, and soft elastic gelatin capsules. Suitable coating materials include pH-sensitive (enteric) materials, which remain intact in the lower pH environs of the stomach and small intestine, but which disintegrate or dissolve at the pH commonly found in the latter portion of the small intestine or beginning of the colon of the patient, typically, a pH above about 6.5.

Preferred enteric coating materials useful for preparing proximal colonic delivery carriers for the unit dosage form compositions of this invention include pH-sensitive polymers which do not dissolve in the lower pH environs of the stomach and the upper portions of the small intestine (pHs lower than about 6.5), but which disintegrate or dissolve at the pH commonly found in the latter portions of the small intestine or in the proximal region of the colon, e.g., above pH 6.5. Such polymers include polymethacrylates (e.g., Eudragit® Type S, or combinations of Eudragit® Types L and S, Rohm Pharma, Darmstadt, West Germany), hydroxypropyl methylcellulose phthalate, shellac, and polyvinyl acetate phthalate. The pH at which such pH-sensitive polymers begin to dissolve and the thickness of coating will determine the site in the intestinal lumen at which the sennosides matrix is released. Typically, higher pH dissolution points and increased amounts of pH-sensitive polymer will increase the distance the unit dosage form will travel in the small intestine and colon prior to release of the sennosides. For certain compositions of this invention, preferred pH-sensitive enteric materials dissolve only at a pH of greater than about 6.5, more preferred enteric materials dissolve only at pH of greater than about 6.8; also preferred are enteric materials which dissolve only at a pH of greater than about 7. An especially preferred pH-sensitive material is a polymethacrylate polymer (Eudragit® S) with a pH dissolution value of about pH 7.

Time-dependent Release Materials

The second preferred proximal colonic delivery carrier is prepared by coating a conventional tablet, hard gelatin capsule, or soft gelatin capsule incorporating the sennosides matrix with a time dependent-release material which remain intact in the lower pH environs of the stomach, but dissolves slowly as the dosage forms passes through the small intestine, followed by a coating of an enteric material which dissolves/disperses when the dosage form enters the upper small intestine (duodenum). The enteric outer coating layer primarily prevents initiation of dissolution/dispersion of the underlying time dependent-release coating within the stomach. The time dependent-release material further delays the release of the sennosides matrix until the dosage form reaches a point near the junction of the small intestine and colon, or within the colon, based upon its dissolution rate and thickness and the intestinal transit rate.

Suitable coatings can also be made of materials which are affected little by changes in pH, but which dissolve or erode slowly as the dosage form passes through the gastrointestinal tract; the thickness of the coating is selected such that the coating breeches, releasing the sennosides matrix, after the time required for the dosage form to travel approximately to the colon. Coatings made from materials or mixtures of materials which combine aspects of the pH-release and time dependent-release mechanisms described below are also suitable.

Technologies suitable for achieving the desired results, such as those described in the two preceding paragraphs, are described by Klaus Lehmann, PRACTICAL COURSE IN LACQUER COATING, Röhm Pharma GmbH, Weiterstadt Germany (1989); and in Eudragit® Technical Data Sheets published by Röhm Pharma GmbH (1991), both incorporated herein by reference.

Preferred time dependent-release coating materials include cellulosic derivatives, such as methyl cellulose, carboxymethyl cellulose, hydroxyethyl cellulose, hydroxypropyl cellulose, and hydroxypropyl methylcellulose. The dissolution rate of these and other time dependent-release materials is largely pH independent and will be a function of molecular weight and degree of substituent substitution. The thickness of the layer of timed-release material, coating conditions, and type and level of coating aids may also influence the rate of dissolution. The rate of dissolution of the time dependent-release material in combination with the intestinal transit rate of the dosage form will control the site in the intestinal lumen at which the sennosides matrix is released.

Preferred enteric coating materials suitable for compositions of the preceding paragraph include pH-sensitive polymers, such as polymethacrylates (e.g., Eudragit Types L and L-55, Rohm Pharma, Darmstadt, West Germany), cellulose acetate phthalate, hydroxypropyl methylcellulose phthalate, and polyvinyl acetate phthalate, which are insoluble at the pH of the gastric environment, but will dissolve at various pH's above about pH 5 and less than about 6.5. The purpose of the enteric coating of these compositions is to delay the start of dissolution/erosion of the time dependent-release coating until the dosage form has emptied from the stomach.

Coating aids such as plasticizers and talc may be incorporated into both sods of coating compositions—both pH-sensitive enteric coatings and time-dependent release coatings. Compressed tablets, and soft and hard gelatin capsules are typically coated in fluidized bed equipment. Tablets and capsules are also typically coated in perforated pans. Tablets may also be coated via compression coating.

Pulse Capsules

The third preferred proximal colonic delivery carrier of this invention is a pulse capsule, such as Pulsincap®. As used herein, "pulse capsules" include capsules described in U.K. Patent Application Nos. 2,230,441A and 2,230,442A of National Research Development Corporation, published Oct. 24, 1990; and PCT Patent Application No. WO 91/12795 of National Research Corporation, published Sep. 5, 1991, all of which have U.S. patent application equivalents and are incorporated herein by reference. One form of such a capsule is Pulsincap® manufactured by Scherer DDS, Clydesbanke, Scotland, U.K.

Preferred pulse capsules comprise a water-insoluble male capsule shell, a water-dispersible or swellable hydrophilic plug, and a water-soluble female capsule shell. The mate and female shells preferably have the size, shape, and fit of conventional hard gelatin capsule male and female mating shells.

For preferred pulse capsule unit dosage form compositions of this invention, the sennosides matrix is contained in the male capsule shell and enclosed with the hydrophilic plug such that the hydrophilic plug blocks the entire opening of the male shell. The female shell covers the exposed portion of the plug and extends along the outer cylindrical surface of the male shell.

In contact with the fluids of the stomach and the intestines beyond, the female shell of a pulse capsule dissolves and the hydrophilic plug hydrates. The composition and size of the hydrophilic plug is selected such that the hydrophilic plug will disengage from the male capsule shell after a predetermined amount of time, releasing the sennosides matrix at the approximate time when the dosage form reaches the colon.

A preferred pulse capsule proximal colonic delivery carrier additionally comprises a pH sensitive material that will dissolve at a pH typically associated with the upper small intestine (duodenum). This coating encompasses the capsule such that the female capsule shell does not dissolve, and hydration of the hydrophilic plug does not begin until the unit dosage form has emptied from the stomach. This controlled delay eliminates variability due to differences in gastric emptying time (time between ingestion of the unit dosage form and its being emptied from the stomach) when determining the amount of time desired between dissolution of the female shell and disengagement of the plug from the male shell opening.

A preferred composition of this invention include the incorporation of sennosides matrix into a Pulsincap® capsule onto which an enteric coating of the type described in the preceding paragraph is applied.

Optional Ingredients

The compositions of this inventions can optionally include active drug ingredients in addition to sennosides. Non-limiting examples of other active drug agents and amounts typically present in such compositions include the following: ducosate sodium, calcium or potassium, from about 5 mg to about 500 rag, preferably from about 50 mg to about 250 rag; glycyrrhiza extract comprising from about 5% to about 30%, preferably from about 10% to about 16%, glycyrrhizic acid, from about 2 mg to about 200 rag, preferably from about 20 mg to about 100 rag.

Methods

Another aspect of this invention is methods for providing laxation for humans and animals in need thereof by peroral administration of the abovedescribed compositions. Conditions for which such laxation may beneficially be provided include the following: constipation, adjunctive therapy for constipation associated with irritable bowel syndrome, and bowel cleansing prior to diagnostic or surgical procedures.

An advantage of providing sennosides to patients using the compositions of this invention is that laxation benefits are generally achieved with diminished secondary diarrhea relative to that commonly associated with conventional sennosides compositions. Another advantage is that such laxation benefits are often achieved more quickly than with conventional sennosides compositions. Another advantage is that a lesser dosage amount of sennosides is needed to achieve laxation than is needed with conventional sennosides compositions. Another advantage is that due to the lesser dosage amount and the more prompt onset of laxation activity, the side effects of cramping and pain are lessened.

Dosages of the compositions of this invention described herein above are preferably administered when laxation is needed. One dose is often sufficient to provide the needed laxation, but several dosages can be used sequentially when needed. Such sequential doses are preferably provided to a patient from about 8 hours to about 24 hours apart, up to a maximum of about 4 such dosages. Typically, a single dose of sennosides invokes laxation.

The following non-limiting examples provide typical formulations for compositions of this invention, and typical methods for treating human disorders with such compositions.

Example 1

| Sennosides matrix | | Proximal colonic delivery carrier | |
|---|---|---|---|
| Component | mg/unit dose | Component | mg/unit dose |
| Sennosides | 10.0 | Polymethacrylates (Eudragit S-100) | 8.7 |
| Lactose | 0.5 | Dibutyl Phthalate | 1.7 |
| Dextrates | 25.0 | Talcum | 2.3 |
| Crospovidone | 5.0 | Ferric Oxide | 1.3 |
| Croscarmellose | 5.0 | | |
| Pregelatinized Starch | 15.0 | | |
| Microcrystalline cellulose | 48.1 | | |
| Magnesium Stearate | 0.4 | | |

Sennosides Matrix

Sennosides is mixed with dextrates followed by addition of a preblended mixture of microcrystalline cellulose, crospovidone, croscarmellose, pregelatinized starch, and fumed silica. Magnesium stearate is then added to the mixture with additional mixing. The resulting powder blend is compressed into tablets.

Proximal Colonic Delivery Carrier

Eudragit S-100 and dibutyl phthalate are dissolved into 85 parts isopropyl alcohol. Talcum and ferric oxide are subsequently added to the solution followed by homogenization. The resulting suspension is then applied to the compressed tablets of the sennosides matrix using a perforated pan coater.

Example 2

| Sennosides matrix | | Proximal colonic delivery carrier | |
|---|---|---|---|
| Component | mg/unit dose | Component | mg/unit dose |
| Sennosides | 10.0 | Polymethacrylates (Eudragit S-100) | 8.7 |
| Lactose | 0.2 | Dibutyl Phthalate | 1.7 |
| Dextrates | 25.0 | Talcum | 2.3 |
| | | Ferric Oxide | 1.3 |

Sennosides Matrix

Sennosides is blended with dextrates and filled into a hard gelatin capsule.

Proximal Colonic Delivery Carrier

Eudragit S-100 and dibutyl phthalate are dissolved into 86 pads isopropyl alcohol. Talcum and ferric oxide are subsequently added to the solution followed by homogenization. The resulting suspension is then applied to the hard gelatin capsules of the sennosides matrix using a perforated pan coater.

Example 3

| Sennosides matrix | | Proximal colonic delivery carrier | |
|---|---|---|---|
| Component | mg/unit dose | Component | mg/unit dose |
| Sennosides | 10.0 | Pulsincap® Capsule | 1 capsule |
| Lactose | 0.5 | Cellulose Acetate Phthalate | 5.0 |
| Dextrates | 25.0 | Castor Oil | 1.2 |
| Crospovidone | 5.0 | | |
| Croscarmellose | 5.0 | | |
| Pregelatinized Starch | 15.0 | | |
| Microcrystalline cellulose | 48.1 | | |
| Magnesium Stearate | 0.4 | | |

Sennosides Matrix

Sennosides is mixed with dextrates followed by addition of a preblended mixture of microcrystalline cellulose, crospovidone, croscarmellose, pregelatinized starch, and fumed silica. Magnesium stearate is then added to the mixture with additional mixing.

Proximal Colonic Delivery Carrier

The sennosides matrix is filled into a Pulsincap® capsule configured to release its contents approximately six hours following contact with the contents of the gastrointestinal tract. Cellulose acetate cellulose and castor oil are dissolved into 85 parts acetone and the resulting solution is applied to the Pulsincap® capsules of the sennosides matrix using a perforated pan coater.

While particular embodiments of this invention have been described, it will be obvious to those skilled in the art that various changes and modifications of this invention can be made without departing from the spirit and scope of the invention. It is intended to cover, in the appended claims, all such modifications that are within the scope of this invention.

What is claimed is:

1. A pharmaceutical laxative composition in unit dosage form, for peroral administration of sennosides to a human or other animal subject, comprising:

(a) from about 3 mg to 25 mg of sennosides contained in a rapidly dissolving matrix; and (b) a proximal colonic delivery carrier which effects release of said sennosides near the junction between the small intestine and the colon or within the colon of said subject, wherein the proximal colonic delivery carrier is selected from the group consisting of pH sensitive enteric material. S, pulse capsules and time dependent-release coating materials, and wherein the sennoside matrix completely dissolves within about 1 to 20 minutes after the proximal colonic delivery carrier begins dissolving.

2. The composition of claim 1 wherein the sennosides matrix comprises 3 mg to about 15 mg of sennosides.

3. The composition of claim 2 wherein the sennosides matrix is in the form of a compressed tablet.

4. The composition of claim 2 wherein the sennosides matrix is in the form of a solids-filled hard gelatin capsule.

5. The composition of claim 2 wherein the proximal colonic delivery carrier comprises a pulse capsule.

6. The composition of claim 1 wherein the sennosides matrix comprises from about 3 mg to about 15 mg of sennosides wherein the sennosides are in a solid dispersion in a water-soluble carrier selected from the group consisting of polyethylene glycol having a molecular weight greater than about 1000 daltons, poloxamer, citric acid, tartaric acid, dextrose monohydrate, and urea.

7. The composition of claim 1 wherein the sennosides matrix comprises from about 3 mg to about 15 mg of sennosides in solution in a water-miscible, pharmaceutically-acceptable solvent that is liquid at about 37° C.

8. The composition of claim 7 wherein the sennosides matrix is encased in a soft gelatin capsule.

9. The composition of claim 1 wherein the proximal colonic delivery carrier comprises a pH-sensitive enteric material which dissolves at a pH of from about 6.5 to about 7.

10. The composition of claim 9 wherein the proximal colonic delivery carrier comprises a pH-sensitive enteric material which dissolves at a pH of about 7.

11. A method for providing laxation for humans and animals in need thereof by peroral administration of the composition of claim 1.

12. A method for providing laxation for humans in need thereof by peroral administration of the composition of claim 9.

* * * * *

UNITED STATES PATENT AND TRADEMARK OFFICE
CERTIFICATE OF CORRECTION

PATENT NO. : 5,514,663
DATED : May 7, 1996
INVENTOR(S) : Kenneth G. Mandel

It is certified that error appears in the above-identified patent and that said Letters Patent is hereby corrected as shown below:

Column 1, line 35 "Casennosides" should read --Ca-sennosides--.
Column 1, line 39 "convened" should read --converted--.
Column 2, lines 42 and 43, and Column 6, lines 59, 60, 62 and 63 "rag" should read --mg--.
Column 2, line 51 and Column 8, line 21 "pads" should read --parts--.
Column 6, line 16 "mate" should read --male--.
Column 7, line 1 "abovedescribed" should read --above described--.
(Claim 1) Column 9, line 12 "material. S," should read --materials,--.
(Claim 1) Column 9, lines 15 and 16 "begins dissolving" should read --dissolves--.
(Claim 6) Column 9, line 26 and (Claim 7) Column 10, line 6 "about" should be deleted.

Signed and Sealed this

Twenty-fifth Day of March, 1997

*Attest:*

BRUCE LEHMAN

*Attesting Officer*   Commissioner of Patents and Trademarks